(12) United States Patent
Tomita et al.

(10) Patent No.: US 9,023,947 B2
(45) Date of Patent: May 5, 2015

(54) CARRIER FOR ADSORPTION AND METHOD FOR PRODUCING SAME

(75) Inventors: Naotoshi Tomita, Otsu (JP); Yoshiyuki Ueno, Otsu (JP)

(73) Assignee: Toray Industries, Inc. (JP)

( * ) Notice: Subject to any disclaimer, the term of this patent is extended or adjusted under 35 U.S.C. 154(b) by 0 days.

(21) Appl. No.: 14/236,989

(22) PCT Filed: Aug. 8, 2012

(86) PCT No.: PCT/JP2012/070146
§ 371 (c)(1),
(2), (4) Date: Feb. 4, 2014

(87) PCT Pub. No.: WO2013/022012
PCT Pub. Date: Feb. 14, 2013

(65) Prior Publication Data
US 2014/0206818 A1 Jul. 24, 2014

(30) Foreign Application Priority Data

Aug. 9, 2011 (JP) ................................. 2011-173774

(51) Int. Cl.
| | |
|---|---|
| *C08K 5/07* | (2006.01) |
| *C08L 9/00* | (2006.01) |
| *C08F 283/00* | (2006.01) |
| *B01J 20/26* | (2006.01) |
| *B01J 20/30* | (2006.01) |
| *A61K 47/00* | (2006.01) |
| *A61K 38/00* | (2006.01) |

(52) U.S. Cl.
CPC ................ *B01J 20/267* (2013.01); *B01J 20/26* (2013.01); *B01J 20/30* (2013.01); *A61K 38/00* (2013.01); *A61K 47/00* (2013.01)

(58) Field of Classification Search
CPC .......... B01J 20/26; B01J 20/30; B01J 20/267; A61K 47/00; A61K 38/00
USPC .................................. 525/153, 164, 154, 534
See application file for complete search history.

(56) References Cited

U.S. PATENT DOCUMENTS 4,225,687 A * 9/1980 deTorres ....................... 525/423
2009/0275874 A1 11/2009 Shimagaki et al.

FOREIGN PATENT DOCUMENTS

| JP | 49-130969 A | 12/1974 |
|---|---|---|
| JP | 49-130969 | 12/1975 |
| JP | 04-185624 A | 7/1992 |
| JP | 2000-044668 A | 2/2000 |
| JP | 2005-082933 A | 3/2005 |
| JP | 2006-272075 A | 10/2006 |
| JP | 2006-312804 A | 11/2006 |
| JP | 2008-080114 A | 4/2008 |
| JP | 4591974 B2 | 9/2010 |
| WO | 2008/047514 A1 | 4/2008 |

* cited by examiner

*Primary Examiner* — William Cheung
(74) *Attorney, Agent, or Firm* — DLA Piper LLP (US)

(57) ABSTRACT

An adsorptive carrier includes one or more high-molecular-weight compounds each of which includes two or more aromatic ring-containing repeating units, the aromatic rings being covalently bound to each other via a structure represented by Formula (I):

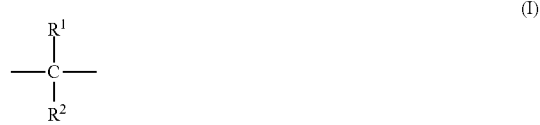

wherein $R^1$ represents hydrogen or an organic group, and $R^2$ represents an organic group.

8 Claims, No Drawings

CARRIER FOR ADSORPTION AND METHOD FOR PRODUCING SAME

This application is the U.S. National Stage under 35 USC 371 of PCT Application PCT/JP2012/070146 with an international filing date of Aug. 8, 2012. The application claims foreign priority on Japan patent application 2011-173774 filed on Aug. 9, 2011.

TECHNICAL FIELD

This disclosure relates to an adsorptive carrier and a method of producing it.

BACKGROUND

Inflammatory cytokines are deeply involved in the causes of inflammatory diseases such as systemic lupus erythematosus, rheumatoid arthritis, multiple sclerosis, ulcerative colitis and Crohn's disease. Therefore, in therapeutic methods for these inflammatory diseases, inactivation of inflammatory cytokines by administration of a biologic such as a low-molecular-weight pharmaceutical or antibody has been attempted. On the other hand, to solve problems such as the increasing cost and induction of an unexpected immune reaction in such pharmacotherapies, therapies by extracorporeal circulation of blood using a column filled with a material having affinity to inflammatory cytokines have been developed in recent years.

As materials having affinity to inflammatory cytokines, adsorptive carriers prepared by immobilizing a functional group comprising an amino group derived from polyamine or the like on the surface of a water-insoluble carrier are known (JP 4591974 B and JP 2006-272075 A). Further, a multifunctional adsorptive carrier that enables adsorptive removal of not only inflammatory cytokines but also activated leukocytes from blood, which carrier is in the form of a fiber and has a diameter within a certain range, is known (JP 2006-312804 A).

Preparation of such a conventional carrier for adsorption of inflammatory cytokines requires a multistep process wherein, for example, polystyrene is first reacted with N-methylol-α-chloroacetamide for introduction of a reactive functional group, and polyamine is then immobilized to the reactive functional group by covalent bonding, to construct a desired functional group on the surface of a water-insoluble carrier. It has been suggested that the functional group immobilized on the surface of the water-insoluble carrier preferably comprises a functional group capable of hydrogen bonding such as a urea bond, thiourea bond and/or amide group. Further, for the purpose of giving solvent resistance and heat resistance to the obtained carrier, cross-linking between benzene rings derived from polystyrene is performed using paraformaldehyde.

However, since a urea bond, thiourea bond and amide group may be hydrolyzed at high temperature, it has been difficult to secure high adsorption capacity by contribution of these functional groups while securing heat resistance of the carrier. Further, although the problem of heat resistance is reduced by cross-linking between benzene rings, the cross-linking reaction and the introduction of a reactive functional group may compete with each other when these are carried out at the same time, resulting in inhibition of the introduction of a reactive functional group. Hence, in a decreased adsorption capacity, and it has also been pointed out that there is the risk of production of unexpected by-products in such a case.

The cross-linking reaction may be carried out as a separate step to avoid the reaction competition, but this increases the number of steps and requires large amounts of various reagents, so that this is not an effective solution at present.

It could therefore be helpful to provide an adsorptive carrier having remarkable blood component-adsorbing capacity, especially inflammatory cytokine-adsorbing capacity, irrespective of whether the carrier has an amide group and/or the like, which carrier also has high solvent resistance and heat resistance. It could also be helpful to provide a method of producing an adsorptive carrier, wherein introduction of a desired functional group on the surface of the carrier and cross-linking between aromatic rings can be achieved by a single step.

SUMMARY

We discovered that use of an aldehyde or ketone having a desired functional group enables high-efficiency adsorption removal of blood components, especially inflammatory cytokines, and achievement of production of an adsorptive carrier having high solvent resistance and heat resistance.

We thus provide the adsorptive carriers and methods of producing them according to (1) to (9):

(1) An adsorptive carrier composed of one or more high-molecular-weight compounds each of which comprises two or more aromatic ring-containing repeating units, the aromatic rings being covalently bound to each other via the structure represented by Formula (I):

wherein $R^1$ represents hydrogen or an organic group, and $R^2$ represents an organic group.

(2) The adsorptive carrier according to (1), wherein the change in the mass of the adsorptive carrier due to immersion in 100 volumes of a good solvent at 25° C. for 20 hours is less than 10% as compared to the mass of the adsorptive carrier before the immersion.

(3) The adsorptive carrier according to (1) or (2), wherein the organic group comprises a substituent selected from the group consisting of an amino group, carboxyl group and sulfonyl group.

(4) The adsorptive carrier according to any one of claims 1 to 3, wherein the $R^1$ is hydrogen.

(5) The adsorptive carrier according to any one of (1) to (4), wherein the high-molecular-weight compound comprises two or more benzene rings.

(6) The adsorptive carrier according to any one of (1) to (5), wherein the high-molecular-weight compound is selected from the group consisting of polystyrene, polysulfone, polyethersulfone and polycarbonate.

(7) The adsorptive carrier according to any one of (1) to (6), which is for adsorption of an inflammatory cytokine(s).

(8) A method for producing an adsorptive carrier, the method comprising a cross-linking step of reacting one or more high-molecular-weight compounds each of which comprises two or more aromatic ring-containing repeating units, with the compound represented by Formula (II) and an acid catalyst, to obtain an adsorptive carrier in which the aromatic rings are covalently bound to each other via the structure represented by Formula (I):

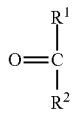
(II)

wherein $R^1$ represents hydrogen or an organic group, and $R^2$ represents an organic group;

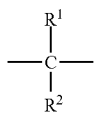
(I)

wherein $R^1$ represents hydrogen or an organic group, and $R^2$ represents an organic group.

(9) The production method according to (8), wherein the organic group is selected from the group consisting of an amino group, carboxyl group and sulfonyl group;
the $R^1$ is hydrogen;
the aromatic ring is a benzene ring; and
the high-molecular-weight compound is selected from the group consisting of polystyrene, polysulfone, polyethersulfone and polycarbonate.

We also provide the adsorptive carriers and the methods of producing them according to (10) to (17):

(10) An inflammatory cytokine-adsorbing carrier composed of a high-molecular-weight compound comprising two or more benzene rings, the benzene rings being covalently bound to each other via the structure represented by Formula (I):

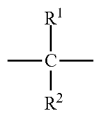
(I)

wherein $R^1$ represents hydrogen or an organic group, and $R^2$ represents an organic group.

(11) The carrier according to (10), wherein the organic group comprises a substituent selected from the group consisting of an amino group, carboxyl group and sulfonyl group.
(12) The carrier according to (10) or (11), wherein the $R^1$ is hydrogen.
(13) The carrier according to (12) or (13), wherein the high-molecular-weight compound is a high-molecular-weight compound selected from the group consisting of polystyrene, polysulfone, polyethersulfone and polycarbonate.
(14) A method for producing an inflammatory cytokine-adsorbing carrier, the method comprising a cross-linking step of reacting a high-molecular-weight compound comprising two or more benzene rings with the compound represented by Formula (II) and an acid catalyst, to obtain an inflammatory cytokine-adsorbing carrier in which the benzene rings are covalently bound to each other via the structure represented by Formula (I):

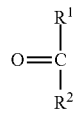
(II)

wherein $R^1$ represents hydrogen or an organic group, and $R^2$ represents an organic group;

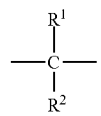
(I)

wherein $R^1$ represents hydrogen or an organic group, and $R^2$ represents an organic group.

(15) The production method according to (14), wherein the organic group comprises a substituent selected from the group consisting of an amino group, carboxyl group and sulfonyl group.
(16) The production method according to (14) or (15), wherein the $R^1$ is hydrogen.
(17) The production method according to any one of (14) to (16), wherein the high-molecular-weight compound is a high-molecular-weight compound selected from the group consisting of polystyrene, polysulfone, polyethersulfone and polycarbonate.

The adsorptive carrier has high heat resistance and can exert remarkable blood component-adsorbing capacity, especially inflammatory cytokine-adsorbing capacity, irrespective of whether the carrier has an amide group and/or the like. Further, the production method can solve many problems such as the requirement of large amounts of various reagents and deterioration of the carrier by the multistep process, and the difficulty in controlling the reaction due to competing reaction.

DETAILED DESCRIPTION

The adsorptive carrier is composed of one or more high-molecular-weight compounds each of which comprises two or more aromatic ring-containing repeating units, which aromatic rings are covalently bound to each other via the structure represented by Formula (I):

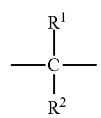
(I)

wherein $R^1$ represents hydrogen or an organic group, and $R^2$ represents an organic group.

The term "high-molecular-weight compound which comprises two or more aromatic ring-containing repeating units" means a high-molecular-weight compound comprising an aromatic ring in a part of the repeat structure of the highmolecular-weight compound. In particular, the compound wherein the aromatic ring is limited to a benzene ring, that is, the "high-molecular-weight compound which comprises two or more benzene rings" means a high-molecular-weight compound comprising a benzene skeleton in a part of the repeat structure of the high-molecular-weight compound, which may be either a homopolymer or copolymer. The "aromatic ring" is not limited, and examples of the aromatic ring include benzenoid aromatic rings such as benzene, naphthalene and anthracene; heteroaromatic rings such as furan, thiophene and pyrrole; and non-benzenoid aromatic rings such as azulene and cyclopentadiene. Examples of the "high-molecular-weight compound which comprises two or more aromatic ring-containing repeating units" and the "high-molecular-weight compound which comprises two or more benzene rings" include polystyrene, polysulfone, polyethersulfone, polyetherketone, polycarbonate and polyethylene terephthalate; and block copolymers, mixtures and polymer alloys among these high-molecular-weight compounds, and between these high-molecular-weight compounds and other high-molecular-weight compounds. Polystyrene, polysulfone, polyethersulfone and polycarbonate are preferred since their performance has been shown in uses in extracorporeal circulation of blood.

The term "aromatic rings are covalently bound to each other via the structure represented by Formula (I)" means a state where an aromatic ring contained in the high-molecular-weight compound is chemically linked by covalent bonding to another aromatic ring contained in the high-molecular-weight compound via the structure represented by Formula (I), that is, a state where an aromatic ring contained in the high-molecular-weight compound is cross-linked with another aromatic ring contained in the high-molecular-weight compound via the structure represented by Formula (I).

Similarly, the term "benzene rings are covalently bound to each other via the structure represented by Formula (I)" means a state where a benzene ring contained in the high-molecular-weight compound is chemically linked by covalent bonding to another benzene ring contained in the high-molecular-weight compound via the structure represented by Formula (I), that is, a state where a benzene ring contained in the high-molecular-weight compound is cross-linked with another aromatic ring contained in the high-molecular-weight compound via the structure represented by Formula (I).

Such cross-linking is not necessarily required for all aromatic rings or benzene rings contained in the high-molecular-weight compound, and the compound may be in a state where only a part of the aromatic rings or benzene rings are cross-linked as described above.

The term "organic group" means an atomic group constituted by elements selected from the group consisting of carbon, hydrogen, oxygen, nitrogen, sulfur and halogens, and examples of the organic group include atomic groups comprising alkyl, phenyl, hydroxyl, mercapto, amino, carboxyl, aldehyde and/or sulfonyl. For exertion of blood component-adsorbing capacity, especially inflammatory cytokine-adsorbing capacity by electrostatic interactions, the organic group preferably comprises a substituent selected from the group consisting of amino, carboxyl and sulfonyl.

The term "adsorptive carrier" means a material that is capable of removing a physiologically active substance(s) such as a protein(s), sugar chain(s) and/or lipid(s) in a liquid by adsorption, and the term "adsorption" means a state where a physiologically active substance(s) such as a protein(s), sugar chain(s) and/or lipid(s) is/are adsorbed to the adsorptive carrier and hardly detached therefrom.

The term "blood component-adsorbing carrier" means a material that is capable of removing a blood component(s) from blood by adsorption.

The term "blood component" means a component constituting blood, and examples of the blood component include blood cell components such as erythrocytes, leukocytes and platelets; and humoral factors such as inflammatory cytokines. In cases where the purpose is treatment of an inflammatory disease, inflammatory cytokines are preferably removed by adsorption.

The term "inflammatory cytokine-adsorbing carrier" means a material that is capable of removing an inflammatory cytokine(s) from blood by adsorption.

The inflammatory cytokine means a protein that is secreted from cells to transmit information to specific cells, and examples of the inflammatory cytokine include interleukins, tumor necrosis factor-$\alpha$, transforming growth factor $\beta$, interferon-$\gamma$, angiogenic growth factor and immunosuppressive acidic protein.

The interleukin means a cytokine that is secreted by leukocytes and functions in regulation of the immune system, and examples of the interleukin include interleukin-1, interleukin-6 (hereinafter referred to as IL-6), interleukin-8 (hereinafter referred to as IL-8), interleukin-10 and interleukin-17.

Whether the crosslink is present or absent is confirmed by solubility of the compound in a good solvent. When the adsorptive carrier is immersed in 100 volumes of a good solvent for the "high-molecular-weight compound comprising two or more aromatic ring-containing repeating units" at a temperature of 25° C. for 20 hours, the compound is judged as having sufficient cross-linked structures in cases where the change in the weight of the adsorptive carrier due to the immersion is less than 10%. That is, when the adsorptive carrier is immersed in 100 volumes of a good solvent at 25° C. for 20 hours, the mass change due to the immersion is preferably less than 10%.

The term "good solvent" herein means a solvent that causes a weight change of the uncrosslinked "high-molecular-weight compound comprising two or more aromatic ring-containing repeating units" of not less than 10% when the uncrosslinked "high-molecular-weight compound comprising two or more aromatic ring-containing repeating units" is immersed in 100 volumes of the solvent at a temperature of 25° C. for 20 hours. This good solvent varies depending on the type of the "high-molecular-weight compound comprising two or more aromatic ring-containing repeating units" and, for example, in cases where the "high-molecular-weight compound comprising two or more aromatic ring-containing repeating units" is polystyrene, examples of the "good solvent" include chloroform, acetone, dimethylsulfoxide, dimethylacetamide, benzene, toluene and nitrobenzene. In cases where the "high-molecular-weight compound comprising two or more aromatic ring-containing repeating units" is polysulfone, examples of the "good solvent" include chloroform, acetone, dimethylsulfoxide, dimethylacetamide and N-methylpyrrolidone. In cases where the "high-molecular-weight compound comprising two or more aromatic ring-containing repeating units" is polyethersulfone, examples of the "good solvent" include chloroform, acetone, dimethylformaldehyde and dimethylsulfoxide.

The method of producing an adsorptive carrier comprises a cross-linking step of reacting one or more high-molecular-weight compounds each of which comprises two or more aromatic ring-containing repeating units, with the compound represented by Formula (II) and an acid catalyst, to obtain an adsorptive carrier in which the aromatic rings are covalently bound to each other via the structure represented by Formula (I):

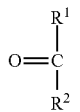
(II)

wherein $R^1$ represents hydrogen or an organic group, and $R^2$ represents an organic group;

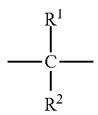
(I)

wherein $R^1$ represents hydrogen or an organic group, and $R^2$ represents an organic group.

The definitions of the terms "high-molecular-weight compound which comprises two or more aromatic ring-containing repeating units" and "high-molecular-weight compound which comprises two or more benzene rings" are the same as described above, and these are again preferably polystyrene, polysulfone, polyethersulfone or polycarbonate.

The compound represented by Formula (II) has an aldehyde group in cases where $R^1$ is hydrogen, or a ketone group in cases where $R^1$ is an organic group, as a result.

The term "acid catalyst" means a Lewis acid, and the acid catalyst is preferably a liquid Lewis acid in view of the simplicity of treatment after the reaction. A Lewis acid soluble in an aprotic solvent is more preferred, and sulfuric acid is still more preferred. Examples of the aprotic solvent include dimethylsulfoxide (hereinafter referred to as DMSO), N,N-dimethylformamide, tetrahydrofuran, acetone, ethyl acetate, nitrobenzene and N-methyl-2-pyrrolidone. The amount of the acid catalyst used in the cross-linking step is preferably 5 to 90% by weight (hereinafter referred to as wt %), more preferably 10 to 80 wt % with respect to the amount of the solvent since in cases where the amount is too small, the reaction efficiency is low, while in cases where the amount is too large, the relative amount of the solvent is low, so that the reaction efficiency is low. The lower limit is preferably 5 wt %, more preferably 10 wt %. The upper limit is preferably 90 wt %, more preferably 80 wt %. Either preferred lower limit may be combined with either preferred upper limit.

The term "carrier in which the aromatic rings are covalently bound to each other via the structure represented by Formula (I)" means a carrier composed of a high-molecular-weight compound(s) wherein an aromatic ring contained in the high-molecular-weight compound is linked to another aromatic ring contained in the high-molecular-weight compound via the structure represented by Formula (I).

The definition of the term "organic group" is the same as described above, and the organic group similarly preferably comprises a substituent selected from the group consisting of amino, carboxyl and sulfonyl.

The reaction mechanism of the high-molecular-weight compound which comprises two or more aromatic ring-containing repeating units or the high-molecular-weight compound which comprises two or more benzene rings with the compound represented by Formula (II) and an acid catalyst in the cross-linking step can be assumed as described below.

First, the acid catalyst causes protonation of the carbonyl oxygen of the compound represented by Formula (II) to produce a carbocation, and substitution of hydrogen in an aromatic ring contained in the high-molecular-weight compound therewith produces the first covalent bond. Further, the acid catalyst causes protonation of the hydroxyl group to cause elimination of a water molecule and production of a carbocation again, leading to substitution of hydrogen in another aromatic ring contained in the high-molecular-weight compound therewith, to produce the second covalent bond.

For efficient proton donation to the compound represented by Formula (II), the solvent used for the cross-linking step is preferably an aprotic polar solvent. On the other hand, in cases where the compound represented by Formula (II) is insoluble in an aprotic polar solvent, a mixed solvent of a protic polar solvent and an aprotic polar solvent may be used. Examples of the protic solvent herein include alcohols such as methanol and ethanol; and acetic acid. In view of the cost, methanol is preferred.

In cases where a mixed solvent of an aprotic solvent and a protic solvent is used, the volume ratio of the aprotic polar solvent is preferably not less than 50 vol %, more preferably not less than 60 vol %.

The reaction temperature in the cross-linking step is not limited as long as the temperature is not less than the freezing point of the mixed solution of the solvent and the catalyst used, and the reaction temperature is preferably not less than 40° C., more preferably not less than 60° C.

The form of the "high-molecular-weight compound which comprises two or more aromatic ring-containing repeating units" or the "high-molecular-weight compound which comprises two or more benzene rings" to be supplied in the cross-linking step is not limited, and, for example, the form of the high-molecular-weight compound may be a fiber or a particle in cases where not only inflammatory cytokines but also their source, activated leukocytes, are to be removed from blood.

In cases where an adsorption capacity for activated leukocytes is to be given to the adsorptive carrier, the "fiber diameter of the fiber" or the "particle diameter of the particle" needs to be "0.5 to 20 µm" for exertion of the phagocytic capacity of the leukocytes. For more stable exertion of the phagocytic capacity of leukocytes, the "fiber diameter of the fiber" or the "particle diameter of the particle" is preferably 4 to 20 µm, more preferably 4 to 10 µm. The phagocytic capacity of leukocytes means the property of granulocytes and monocytes to capture and eat microorganisms and bacteria that invaded into the body of human or the like.

The term "fiber diameter of the fiber" means the mean of values obtained by randomly collecting 10 small pieces of the fiber as samples and taking a photograph of each piece using a scanning electron microscope at a magnification of ×2000, followed by measuring diameters of the samples at 10 positions in each photograph (100 positions in total). Similarly, the term "particle diameter of the particle" means the mean of values obtained by randomly collecting 10 small pieces of the particle as samples and taking a photograph of each piece using a scanning electron microscope at a magnification of ×2000, followed by measuring the diameters of the samples at 10 positions in each photograph (100 positions in total).

In cases where the fiber diameter of the fiber is less than 10 µm, a thicker fiber may be mixed therewith for securing the strength of the inflammatory cytokine-adsorbing carrier, and the fiber diameter of such a thick fiber is preferably 10 to 50 µm.

Examples of the form of the carrier composed of a fiber(s) include woven fabrics, non-woven fabrics, cotton fabrics and hollow fibers. In cases where the carrier is in the form of a non-woven fabric, a scaffold fiber is preferably included therein for retaining the shape of the non-woven fabric.

The shape of the container to be filled with the adsorptive carrier is not limited as long as the container has an inlet and an outlet for blood, and examples of the shape of the container include cylindrical containers, and prism-shaped containers such as triangular prism-shaped, quadrangular prism-shaped, hexagonal prism-shaped and octagonal prism-shaped containers. The container is preferably a container which can be filled with the adsorptive carrier in a laminated form, a container which can be filled with the adsorptive carrier wound in a cylindrical shape, or a container wherein blood flows from the circumference of a cylinder into the inside thereof, followed by flowing to the outside of the container.

The adsorptive carrier can efficiently remove blood components, especially inflammatory cytokines from blood, and can be used as a blood component-adsorbing carrier or an inflammatory cytokine-adsorbing carrier in the field of medicine. Further, the above-described method for producing an adsorptive carrier can be suitably used as a method for producing the blood component-adsorbing carrier or a method for producing the inflammatory cytokine-adsorbing carrier.

EXAMPLES

Our adsorptive carriers and the column filled with the adsorptive carriers are described below more concretely by way of experimental examples.

Preparation of PP Non-Woven Fabric

A sea-island composite fiber having 36 islands each of which further has a core/sheath complex was obtained using the following components under the conditions of a spinning rate of 800 m/minute and a draw ratio of 3:

The core component of the island: polypropylene
The sheath component of the island: 90 wt % polystyrene and 10 wt % polypropylene
The sea component: copolymerized polyester comprising ethylene terephthalate units as major repeating units and 3 wt % 5-sodium sulfoisophthalic acid as a copolymerization component
The composite ratio (weight ratio): core:sheath:sea=45:40:15.

After preparing a non-woven fabric composed of this fiber in an amount of 85 wt % and a polypropylene fiber having a diameter of 20 μm in an amount of 15 wt %, a sheet-shaped polypropylene net (thickness, 0.5 mm; single fiber diameter, 0.3 mm; aperture, 2 mm×2 mm) was sandwiched between two sheets of this non-woven fabric, and the resultant was needle-punched to obtain a non-woven fabric having a three-layer structure (hereinafter referred to as PP non-woven fabric).

Preparation of PSt+PP Non-Woven Fabric

The PP non-woven fabric was treated at 95° C. with 3 wt % aqueous sodium hydroxide solution to dissolve the sea component. A non-woven fabric having a diameter of the core/sheath fiber of 5 μm and a bulk density of 0.02 g/cm³ (PSt+PP non-woven fabric, hereinafter referred to as non-woven fabric A) was thereby prepared.

Preparation of Non-Woven Fabric Using 4-Dimethylaminobenzaldehyde

Forty milliliters of a reaction liquid was prepared by mixing, stirring and dissolving 48.3 wt % nitrobenzene, 48.3 wt % sulfuric acid and 3.4 wt % dimethylaminobenzaldehyde at 50° C. In this reaction liquid, 1 g of the non-woven fabric A was immersed, and the reaction was allowed to proceed for 1.5 hours while the temperature of the reaction liquid was kept at 50° C. Thereafter, the non-woven fabric was removed from the reaction liquid, and washed by immersion in 40 mL of nitrobenzene. Subsequently, the non-woven fabric was removed therefrom and washed by immersion in methanol, further followed by washing by immersion in water, to obtain a non-woven fabric prepared using 4-dimethylaminobenzaldehyde (hereinafter referred to as non-woven fabric B). The structural formula of 4-dimethylaminobenzaldehyde, which was used for covalent bonding between benzene rings in the non-woven fabric B, is shown in Table 1.

Preparation of Non-Woven Fabric Using Terephthalaldehydic Acid

Forty milliliters of a reaction liquid was prepared by mixing, stirring and dissolving 48.3 wt % nitrobenzene, 48.3 wt % sulfuric acid and 3.4 wt % terephthalaldehydic acid at 50° C. In this reaction liquid, 1 g of the non-woven fabric A was immersed, and the reaction was allowed to proceed for 1.5 hours while the temperature of the reaction liquid was kept at 50° C. Thereafter, the non-woven fabric was removed from the reaction liquid, and washed by immersion in 40 mL of nitrobenzene. Subsequently, the non-woven fabric was removed therefrom and washed by immersion in methanol, further followed by washing by immersion in water, to obtain a non-woven fabric prepared using terephthalaldehydic acid (hereinafter referred to as non-woven fabric C). The structural formula of terephthalaldehydic acid, which was used for covalent bonding between benzene rings in the non-woven fabric C, is shown in Table 1.

Preparation of Non-Woven Fabric Using Hydroxybenzaldehyde

Forty milliliters of a reaction liquid was prepared by mixing, stirring and dissolving 48.3 wt % nitrobenzene, 48.3 wt % sulfuric acid and 3.4 wt % hydroxybenzaldehyde at 50° C. In this reaction liquid, 1 g of the non-woven fabric A was immersed, and the reaction was allowed to proceed for 1.5 hours while the temperature of the reaction liquid was kept at 50° C. Thereafter, the non-woven fabric was removed from the reaction liquid, and washed by immersion in 40 mL of nitrobenzene. Subsequently, the non-woven fabric was removed therefrom and washed by immersion in methanol, further followed by washing by immersion in water, to obtain a non-woven fabric prepared using hydroxybenzaldehyde (hereinafter referred to as non-woven fabric D). The structural formula of hydroxybenzaldehyde, which was used for covalent bonding between benzene rings in the non-woven fabric D, is shown in Table 1.

Preparation of Non-Woven Fabric Using 4-(Dimethylamino) Benzophenone

Forty milliliters of a reaction liquid was prepared by mixing, stirring and dissolving 48.3 wt % nitrobenzene, 48.3 wt % sulfuric acid and 3.4 wt % 4-(dimethylamino)benzophenone at 50° C. In this reaction liquid, 1 g of the non-woven fabric A was immersed, and the reaction was allowed to proceed for 1.5 hours while the temperature of the reaction liquid was kept at 50° C. Thereafter, the non-woven fabric was removed from the reaction liquid, and washed by immersion in 40 mL of nitrobenzene. Subsequently, the non-woven fabric was removed therefrom and washed by immersion in methanol, further followed by washing by immersion in water, to obtain a non-woven fabric prepared using 4-(dimethylamino)benzophenone (hereinafter referred to as non-woven fabric E). The structural formula of 4-(dimethylamino)benzophenone, which was used for covalent bonding between benzene rings in the non-woven fabric E, is shown in Table 1.

Preparation of Non-Woven Fabric Using 4-Dimethylaminoacetophenone

Forty milliliters of a reaction liquid was prepared by mixing, stirring and dissolving 48.3 wt % nitrobenzene, 48.3 wt % sulfuric acid and 3.4 wt % 4-dimethylaminoacetophenone at 50° C. In this reaction liquid, 1 g of the non-woven fabric A was immersed, and the reaction was allowed to proceed for 1.5 hours while the temperature of the reaction liquid was kept at 50° C. Thereafter, the non-woven fabric was removed from the reaction liquid, and washed by immersion in 40 mL of nitrobenzene. Subsequently, the non-woven fabric was removed therefrom and washed by immersion in methanol, further followed by washing by immersion in water, to obtain a non-woven fabric prepared using 4-dimethylaminoacetophenone (hereinafter referred to as non-woven fabric F). The structural formula of 4-dimethylaminoacetophenone, which was used for covalent bonding between benzene rings in the non-woven fabric F, is shown in Table 1.

Preparation of Non-Woven Fabric Using 4-Acetaminophen

Forty milliliters of a reaction liquid was prepared by mixing, stirring and dissolving 48.3 wt % nitrobenzene, 48.3 wt % sulfuric acid and 3.4 wt % 4-acetaminophen at 50° C. In this reaction liquid, 1 g of the non-woven fabric A was immersed, and the reaction was allowed to proceed for 1.5 hours while the temperature of the reaction liquid was kept at 50° C. Thereafter, the non-woven fabric was removed from the reaction liquid, and washed by immersion in 40 mL of nitrobenzene. Subsequently, the non-woven fabric was removed therefrom and washed by immersion in methanol, further followed by washing by immersion in water, to obtain a non-woven fabric prepared using 4-acetaminophen (hereinafter referred to as non-woven fabric G). The structural formula of 4-acetaminophen, which was used for covalent bonding between benzene rings in the non-woven fabric G, is shown in Table 1.

Preparation of Non-woven Fabric Using Formaldehyde

Forty milliliters of a reaction liquid was prepared by mixing, stirring and dissolving 48.3 wt % nitrobenzene, 48.3 wt % sulfuric acid and 3.4 wt % paraformaldehyde at 50° C. In this reaction liquid, 1 g of the non-woven fabric A was immersed, and the reaction was allowed to proceed for 1.5 hours while the temperature of the reaction liquid was kept at 50° C. Thereafter, the non-woven fabric was removed from the reaction liquid, and washed by immersion in 40 mL of nitrobenzene. Subsequently, the non-woven fabric was removed therefrom and washed by immersion in methanol, further followed by washing by immersion in water, to obtain a non-woven fabric prepared using formaldehyde (hereinafter referred to as non-woven fabric H). The structural formula of formaldehyde, which was used for covalent bonding between benzene rings in the non-woven fabric D, is shown in Table 1.

Preparation of Non-Woven Fabric without Use of Aldehyde

Forty milliliters of a reaction liquid was prepared by mixing, stirring and dissolving 50 wt % nitrobenzene and 50 wt % sulfuric acid at 50° C. In this reaction liquid, 1 g of the non-woven fabric A was immersed, and the reaction was allowed to proceed for 1.5 hours while the temperature of the reaction liquid was kept at 50° C. Thereafter, the non-woven fabric was removed from the reaction liquid, and washed by immersion in 40 mL of nitrobenzene. Subsequently, the non-woven fabric was removed therefrom and washed by immersion in methanol, further followed by washing by immersion in water, to obtain a non-woven fabric (hereinafter referred to as non-woven fabric I).

Preparation of Hollow Fiber Using 4-Dimethylaminobenzaldehyde

Forty milliliters of a reaction liquid was prepared by mixing, stirring and dissolving 48.3 wt % nitrobenzene, 48.3 wt % sulfuric acid and 3.4 wt % dimethylaminobenzaldehyde at 50° C. In this reaction liquid, 0.5 g of a polysulfone hollow fiber having an outer diameter of 460 µm and inner diameter of 300 µm (Torayvino (registered trademark); Toray Industries, Inc.) was immersed, and the reaction was allowed to proceed for 1.5 hours while the temperature of the reaction liquid was kept at 50° C. Thereafter, the hollow fiber was removed from the reaction liquid, and washed by immersion in 40 mL of nitrobenzene. Subsequently, the hollow fiber was removed therefrom and washed by immersion in methanol, further followed by washing by immersion in water, to obtain a hollow fiber prepared using 4-dimethylaminobenzaldehyde (hereinafter referred to as hollow fiber A).

Preparation of Hollow Fiber without Use of Aldehyde

Forty milliliters of a reaction liquid was prepared by mixing, stirring and dissolving 50 wt % nitrobenzene and 50 wt % sulfuric acid at 50° C. In this reaction liquid, 0.5 g of a polysulfone hollow fiber having an outer diameter of 460 µm and inner diameter of 300 µm (Torayvino (registered trademark); Toray Industries, Inc.) was immersed, and the reaction was allowed to proceed for 1.5 hours while the temperature of the reaction liquid was kept at 50° C. Thereafter, the hollow fiber was removed from the reaction liquid, and washed by immersion in 40 mL of nitrobenzene. Subsequently, the hollow fiber was removed therefrom and washed by immersion in methanol, further followed by washing by immersion in water, to obtain a hollow fiber (hereinafter referred to as hollow fiber B).

TABLE 1

| Non-woven fabric | Compound used |
|---|---|
| Non-woven fabric B | 4-dimethylaminobenzaldehyde |
| Non-woven fabric C | 4-carboxybenzaldehyde |
| Non-woven fabric D | 4-hydroxybenzaldehyde |
| Non-woven fabric E | 4-dimethylaminobenzophenone |
| Non-woven fabric F | 4-dimethylaminoacetophenone |
| Non-woven fabric G | 4-acetaminophen |
| Non-woven fabric H | formaldehyde |

TABLE 1-continued

| Non-woven fabric | Compound used |
| --- | --- |
| Non-woven fabric I | None |
| Hollow fiber | Compound used |
| Hollow fiber A | 4-(dimethylamino)benzaldehyde |
| Hollow fiber B | None |

Example 1

The non-woven fabric B was cut out into 2 disks each having a diameter of 8 mm, and placed in a polypropylene container. To this container, 0.8 mL of fetal bovine serum (hereinafter referred to as FBS) prepared such that each of IL-6 and IL-8 was contained at a concentration of 500 pg/mL was added, and the content of the container was mixed by inversion in an incubator at 37° C. for 1 hour. Thereafter, the remaining concentration of each of IL-6 and IL-8 was measured by the ELISA method, to calculate the adsorption ratios of IL-6 and IL-8 according to Equations 1 and 2, respectively. The results are shown in Table 2.

IL-6 adsorption ratio(%)={(concentration of IL-6 before mixing by inversion)−(concentration of IL-6 after mixing by inversion)}/(concentration of IL-6 before mixing by inversion)×100   Equation 1

IL-8 adsorption ratio(%)={(concentration of IL-8 before mixing by inversion)−(concentration of IL-8 after mixing by inversion)}/(concentration of IL-8 before mixing by inversion)×100   Equation 2

Further, to investigate the solvent resistance of the non-woven fabric B, the non-woven fabric B was dried, and then immersed in a mixed solution of 50 wt % nitrobenzene and 50 wt % sulfuric acid, which is the reaction solvent, for 20 hours. After washing with nitrobenzene, washing with methanol and washing with water, the non-woven fabric B was dried again, while the weight of the non-woven fabric B was measured before and after this second drying. The change in the weight (%) by the second drying was calculated, and when the value was higher than 10%, the non-woven fabric was judged as having no solvent resistance. The results are shown in Table 2.

Example 2

The non-woven fabric C was cut out into 2 disks each having a diameter of 8 mm, and placed in a polypropylene container. To this container, 0.8 mL of FBS prepared such that each of IL-6 and IL-8 was contained at a concentration of 500 pg/mL was added, and the content of the container was mixed by inversion in an incubator at 37° C. for 1 hour. Thereafter, the adsorption ratios of IL-6 and IL-8 were calculated in the same manner as in Example 1. Further, the solvent resistance of the non-woven fabric C was judged in the same manner as in Example 1. The results are shown in Table 2.

Example 3

The non-woven fabric D was cut out into 2 disks each having a diameter of 8 mm, and placed in a polypropylene container. To this container, 0.8 mL of FBS prepared such that each of IL-6 and IL-8 was contained at a concentration of 500 pg/mL was added, and the content of the container was mixed by inversion in an incubator at 37° C. for 1 hour. Thereafter, the adsorption ratios of IL-6 and IL-8 were calculated in the same manner as in Example 1. Further, the solvent resistance of the non-woven fabric D was judged in the same manner as in Example 1. The results are shown in Table 2.

Example 4

The non-woven fabric E was cut out into 2 disks each having a diameter of 8 mm, and placed in a polypropylene container. To this container, 0.8 mL of FBS prepared such that each of IL-6 and IL-8 was contained at a concentration of 500 pg/mL was added, and the content of the container was mixed by inversion in an incubator at 37° C. for 1 hour. Thereafter, the adsorption ratios of IL-6 and IL-8 were calculated in the same manner as in Example 1. Further, the solvent resistance of the non-woven fabric E was judged in the same manner as in Example 1. The results are shown in Table 2.

Example 5

The non-woven fabric F was cut out into 2 disks each having a diameter of 8 mm, and placed in a polypropylene container. To this container, 0.8 mL of FBS prepared such that each of IL-6 and IL-8 was contained at a concentration of 500 pg/mL was added, and the content of the container was mixed by inversion in an incubator at 37° C. for 1 hour. Thereafter, the adsorption ratios of IL-6 and IL-8 were calculated in the same manner as in Example 1. Further, the solvent resistance of the non-woven fabric F was judged in the same manner as in Example 1. The results are shown in Table 2.

Example 6

The non-woven fabric G was cut out into 2 disks each having a diameter of 8 mm, and placed in a polypropylene container. To this container, 0.8 mL of FBS prepared such that each of IL-6 and IL-8 was contained at a concentration of 500 pg/mL was added, and the content of the container was mixed by inversion in an incubator at 37° C. for 1 hour. Thereafter, the adsorption ratios of IL-6 and IL-8 were calculated in the same manner as in Example 1. Further, the solvent resistance of the non-woven fabric G was confirmed in the same manner as in Example 1. The results are shown in Table 2.

Example 7

The hollow fiber A was cut into 200 pieces each having a length of 1 cm (200 cm in total), and placed in a polypropylene container. To this container, 1 mL of FBS prepared such that each of IL-6 and IL-8 was contained at a concentration of 500 pg/mL was added, and the content of the container was mixed by inversion in an incubator at 37° C. for 1 hour. Thereafter, the adsorption ratios of IL-6 and IL-8 were calculated in the same manner as in Example 1. Further, the solvent resistance of the hollow fiber A was confirmed in the same manner as in Example 1. The results are shown in Table 2.

Comparative Example 1

The non-woven fabric H was cut out into 2 disks each having a diameter of 8 mm, and placed in a polypropylene container. To this container, 0.8 mL of FBS prepared such that each of IL-6 and IL-8 was contained at a concentration of 500 pg/mL was added, and the content of the container was mixed by inversion in an incubator at 37° C. for 1 hour. Thereafter, the adsorption ratios of IL-6 and IL-8 were calculated in the same manner as in Example 1. Further, the solvent resistance of the non-woven fabric H was judged in the same manner as in Example 1. The results are shown in Table 2.

Comparative Example 2

The non-woven fabric I was cut out into 2 disks each having a diameter of 8 mm, and placed in a polypropylene container. To this container, 0.8 mL of FBS prepared such that each of IL-6 and IL-8 was contained at a concentration of 500 pg/mL was added, and the content of the container was mixed by inversion in an incubator at 37° C. for 1 hour. Thereafter, the adsorption ratios of IL-6 and IL-8 were calculated in the same manner as in Example 1. Further, the solvent resistance of the non-woven fabric I was judged in the same manner as in Example 1. The results are shown in Table 2.

Comparative Example 3

The hollow fiber B was cut into 200 pieces each having a length of 1 cm (200 cm in total), and placed in a polypropylene container. To this container, 1 mL of FBS prepared such that each of IL-6 and IL-8 was contained at a concentration of 500 pg/mL was added, and the content of the container was mixed by inversion in an incubator at 37° C. for 1 hour. Thereafter, the adsorption ratios of IL-6 and IL-8 were calculated in the same manner as in Example 1. Further, the solvent resistance of the polysulfone hollow fiber was judged in the same manner as in Example 1. The results are shown in Table 2.

TABLE 2

| Example | | IL-6 ADSORPTION RATIO [%] | IL-8 ADSORPTION RATIO [%] | Solvent resistance |
|---|---|---|---|---|
| Example 1 | Non-woven fabric B | 92.4 | 97.5 | Yes |
| Example 2 | Non-woven fabric C | 5.7 | 99.2 | Yes |
| Example 3 | Non-woven fabric D | 4.5 | 65.1 | Yes |
| Example 4 | Non-woven fabric E | 0.11 | 47.0 | Yes |
| Example 5 | Non-woven fabric F | 0.18 | 72.4 | Yes |
| Example 6 | Non-woven fabric G | 0.95 | 89.8 | Yes |
| Example 7 | Hollow fiber A | 82.1 | 84.5 | Yes |
| Comparative Example 1 | Non-woven fabric H | 2.6 | 34.1 | Yes |
| Comparative Example 2 | Non-woven fabric I | 0 | 78.3 | No |
| Comparative Example 3 | Hollow fiber B | 10.6 | 3.7 | No |

From the results in Table 2, it was revealed that our adsorptive carriers show remarkable inflammatory cytokine-adsorbing capacity and solvent resistance.

INDUSTRIAL APPLICABILITY

Our adsorptive carriers can be used as an inflammatory cytokine-adsorbing carrier, in the field of medicine.

The invention claimed is:

1. An adsorptive carrier comprising one or more high-molecular-weight compounds each of which comprises two or more aromatic ring-containing repeating units, said aromatic rings being covalently bound to each other via a structure represented by Formula (I):

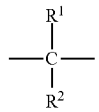

(I)

wherein $R^1$ represents hydrogen or an organic group, $R^2$ represents an organic group, and said organic group comprises a substituent selected from the group consisting of an amino group, carboxyl group and sulfonyl group.

2. The adsorptive carrier according to claim 1, wherein a change in mass of said adsorptive carrier due to immersion in 100 volumes of a good solvent at 25° C. for 20 hours is less than 10% compared to mass of said adsorptive carrier before immersion.

3. The adsorptive carrier according to claim 1, wherein said $R^1$ is hydrogen.

4. The adsorptive carrier according to claim 1, wherein said high-molecular-weight compound comprises two or more benzene rings.

5. The adsorptive carrier according to claim 1, wherein said high-molecular-weight compound is selected from the group consisting of polystyrene, polysulfone, polyethersulfone and polycarbonate.

6. The adsorptive carrier according to claim 1, which adsorbs an inflammatory cytokine(s).

7. A method of producing an adsorptive carrier comprising a cross-linking step of reacting one or more high-molecular-weight compounds each of which comprises two or more aromatic ring-containing repeating units, with a compound represented by Formula (II) and an acid catalyst, to obtain an adsorptive carrier in which said aromatic rings are covalently bound to each other via a structure represented by Formula (I):

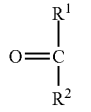

(II)

wherein $R^1$ represents hydrogen or an organic group, and $R^2$ represents an organic group;

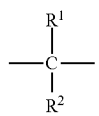

(I)

wherein $R^1$ represents hydrogen or an organic group, and $R^2$ represents an organic group.

8. The method according to claim 7, wherein
said organic group is selected from the group consisting of an amino group, carboxyl group and sulfonyl group;
said $R^1$ is hydrogen;
said aromatic ring is a benzene ring; and
said high-molecular-weight compound is selected from the group consisting of polystyrene, polysulfone, polyethersulfone and polycarbonate.

* * * * *